(12) United States Patent
Barolet

(10) Patent No.: US 9,737,728 B2
(45) Date of Patent: *Aug. 22, 2017

(54) METHOD FOR THE TREATMENT OF MAMMALIAN SKIN TISSUES VIA PULSE IRRADIATION IN THE PRESENCE OF A PHOTOACTIVE COMPOUND

(71) Applicant: Daniel Barolet, Rosemere (CA)

(72) Inventor: Daniel Barolet, Rosemere (CA)

(73) Assignee: 9127-4910 Quebec Inc., Laval (CA)

( * ) Notice: Subject to any disclaimer, the term of this patent is extended or adjusted under 35 U.S.C. 154(b) by 446 days.

This patent is subject to a terminal disclaimer.

(21) Appl. No.: 14/483,675

(22) Filed: Sep. 11, 2014

(65) Prior Publication Data

US 2015/0005692 A1   Jan. 1, 2015

Related U.S. Application Data

(63) Continuation of application No. 11/660,088, filed as application No. PCT/CA2005/001243 on Aug. 15, 2005, now abandoned.

(60) Provisional application No. 60/601,117, filed on Aug. 13, 2004.

(51) Int. Cl.
| | |
|---|---|
| *A61N 5/06* | (2006.01) |
| *A61K 31/375* | (2006.01) |
| *A61K 41/00* | (2006.01) |
| *A61N 5/00* | (2006.01) |

(52) U.S. Cl.
CPC ............ *A61N 5/062* (2013.01); *A61K 31/375* (2013.01); *A61K 41/00* (2013.01); *A61N 2005/007* (2013.01); *A61N 2005/0651* (2013.01); *A61N 2005/0652* (2013.01)

(58) Field of Classification Search
CPC .................. A61N 5/062; A61N 5/0616; A61N 2005/0652; A61N 2005/0651; A61N 2005/0642; A61N 2005/0643; A61N 2005/007; A61K 31/375; A61K 41/00; A61B 18/203; A61B 2018/00452
USPC ................................................. 607/88; 606/9
See application file for complete search history.

(56) References Cited

U.S. PATENT DOCUMENTS

| | | | | |
|---|---|---|---|---|
| 5,632,739 A | * | 5/1997 | Anderson | A61B 18/24 606/15 |
| 5,913,884 A | * | 6/1999 | Trauner | A61B 17/00 607/88 |
| 6,022,455 A | * | 2/2000 | Otake | H05B 37/02 204/157.6 |

(Continued)

*Primary Examiner* — Gary Jackson
*Assistant Examiner* — Boniface N Nganga

(57) ABSTRACT

A method of treating mammalian skin tissues for causing a predetermined physiological change in the mammalian skin tissues. A treatment composition of matter is applied onto the mammalian skin. The mammalian skin is irradiated with a first pulse having a power density above an activation threshold power density and with a second pulse. The first pulse is emitted for a duration of from about 1 femtosecond to about 1 hour, and the first pulse is separated from the second pulse by an inter-pulse interval of from about 1 microsecond to about 10 seconds. The treatment composition of matter includes a photoreactive substance and is applied in an amount sufficient to cause physiological changes within the mammalian skin tissue upon the mammalian skin tissue being irradiated.

16 Claims, 6 Drawing Sheets

(56) References Cited

U.S. PATENT DOCUMENTS

| | | | |
|---|---|---|---|
| 6,595,985 B1 * | 7/2003 | Tobinick | A61B 18/203 606/13 |
| 7,914,523 B2 * | 3/2011 | Barolet | A61B 18/203 128/898 |
| 2003/0004556 A1 * | 1/2003 | McDaniel | A61K 8/494 607/88 |

* cited by examiner

METHOD FOR THE TREATMENT OF MAMMALIAN SKIN TISSUES VIA PULSE IRRADIATION IN THE PRESENCE OF A PHOTOACTIVE COMPOUND

This application is a continuation of U.S. patent application Ser. No. 11/660,088 filed on Feb. 13, 2007, which is a National Phase Entry from PCT Patent Application PCT/CA05/01243, which PCT application claims priority from U.S. Provisional Patent Application Ser. No. 60/601,117 filed Aug. 13, 2004. All these patent applications is hereby incorporated by reference in its entirety.

FIELD OF THE INVENTION

The present invention relates to the field of treatment of living tissue such as the dermatological treatment of skin, and is particularly concerned with a method for the treatment of mammalian skin tissues.

BACKGROUND

The first law of photochemistry states that light has got to be absorbed before photochemistry can occur, which stresses the importance of cellular absorption (Smith, 1981). Typically, photobiological effects are both wavelength and dose-dependent, and result from chemical and/or physical changes induced by non-ionizing radiation (Anderson and Parrish, 1981). When used at a proper wavelength, light activation of enzymes and other tissue components leads to changes in metabolism and induces metabolic modulations.

As light energy is absorbed within the skin, light can be used to achieve desired clinical results. In particular, light has been used to remove vessels, hair, eliminate leg veins, remove or reduce the color of tattoos. In addition, water absorption of light energy transforming light into heat energy has been used for laser ablation of the skin surface or for use of lasers as cutting instruments. Plastic surgeons, dermatologists and their patients continually search for new and improved methods to alter the appearance of the skin.

Since 1970, Low Level Laser Therapy (LLLT), non-thermal, non ablative energy, has been used in phototherapy to speed up wound recovery, to promote angiogenesis and in physiotherapy, to treat musculoskeletal injuries (Basford, 1986; Wheeland, 1993; Conlan et al., 1996; Schindl and Schindl, 2000; Whelan et al., 2001). Light-induced physiological responses can also promote collagen production and accumulation to promote skin appearance and enhancement of skin texture (Yamamoto et al., 1996; Barolet et al., 2005).

The adjustment of various parameters was found to enhance dermal collagen production using non-ablative, non-thermal light source. For instance, specific wavelengths were able to induce increased growth characteristics in fibroblasts (Bosatra et al., 1986; Yamamoto et al., 1996; Almeida-Lopes et al., 2001; Vinck et al., 2003). The fluence, or total dose of energy distributed over a given amount of time, as well as irradiance or the total light intensity reaching the cell are also thought to be involved. In fact, it is suggested that the cellular threshold irradiance would have to be reached to induce a proper physiological stimulation for collagen synthesis within a relatively narrow window of opportunity (Sommer et al., 2001).

Fluence and irradiance are independent variables to be considered in order to generate a specific physiological effect, as even prolonged but insufficient irradiance exposure could have no physiological benefit if the irradiance threshold is not surpassed (Sommer et al., 2001). Finally, pulse duration in microsecond domains that demonstrated an increase in dermal collagen with the pulsed dye laser at 585 nm in earlier studies (Bjerring et al., 2002; Moody et al., 2003) is applied to LED science and pulsing patterns are being elaborated to increase cellular stimulation (Weiss et al., 2005; Barolet et al., 2005).

Photochemistry/biology happens when a chromophore absorbs light energy. The chromophore can be a true color pigment such as black, brown, or red pigments, or a molecule absorbing energy, such as water or a protein complex. Selective chromophore absorption is the absorption of a particular type of light energy by a chromophore. A clinical light treatment typically works because of selective chromophore absorption, wherein light energy is selectively absorbed by a particular component of the skin.

It has been proposed that light-activated enzymes of respiratory chains like mitochondrial NADH-dehydrogenase, and cytochrome c oxidase could act as photoacceptors promoting mitochondrial redox activity and cellular redox state (Karu, 1999; 2004). Therefore, the dermal fibroblast mitochondrial cytochrome c oxidase is thought to act as an endogenous chromophore. Light activation of cellular component at a proper wavelength was found to induce metabolic modulations correlating with tissue response (Smith, 1981; Anderson et al., 1981; Bihari and Mester, 1989; Yu et al., 1994; Almeida-Lopes et al., 2001 Wheeland et al., 2001). Wavelengths around 660 nm were found to reach through the whole papillary layer to enhance collagen production (Webb et al., 1998,). Such non-thermal non-ablative light treatment mainly targets the dermal fibroblast to enhance collagen production and improve skin texture. However it has little or no effects on the epidermis.

PhotoDynamic Therapy (PDT) is another way to use light to enhance skin appearance. However, PDT typically involves the application of a topical photosensitizer that once activated by irradiation induces tissue necrosis. Necrosis results from selective accumulation of the activated photosensitizer in diseased tissue, which generates free radicals. First used as a treatment modality for various cancers, PDT is nowadays undergoing rapid development for cosmetic applications. Indeed, PDT is emerging as a powerful new tool to boost clinical results of non-ablative laser and/or light therapy in the treatment of aged and sun damaged skin, as well as acne. The application of a light-sensitizing solution to skin marred by scaly lesions, skin blotchiness and enlarged pores, followed by the delivery of a light treatment appears to enhance cosmetic skin appearance by improving skin tone, skin texture and pore size. However downtime must still be anticipated, such as redness, crust or more severe side effects that demands longer recovery time.

The epidermis is also targeted to enhance skin general appearance. It has been found that retinol, retinol derivatives, pentapeptides and copper peptides have enhanced efficacy to affect cellular proliferation and differentiation, having a surprising effect in reducing signs of photodamage or aging skin (appearance of fine lines) hyperpigmentation and age spots. Topical creams promote flexibility of the stratum corneum, increasing the content of collagen, and/or glycosaminoglycans in skin, increasing skin moisture, and decreasing transcutaneous water loss to obtain enhanced global skin appearance.

However, some powerful topical agents can irritate the skin. For example, tretinoin used in potent anti-wrinkling regimens and proven to stimulate collagen production in the dermis but may cause erythema, reducing compliance to the treatment. Moreover, light-based techniques used to enhance skin appearance typically target dermal fibroblasts but have little effect on the epidermis.

In view of the above, there is a need in the industry to provide a novel method for the treatment of mammalian skin tissues.

An object of the present invention is therefore to provide a novel method for the treatment of mammalian skin tissues.

The present description refers to a number of documents, the content of which is herein incorporated by reference in their entirety.

SUMMARY OF THE INVENTION

In a broad aspect, the invention provides a method of treating mammalian skin tissues for causing a predetermined physiological change in the mammalian skin tissues. The method includes: applying onto the mammalian skin tissues a treatment composition of matter; irradiating the mammalian skin tissues with a first pulse having a power density above an activation threshold power density; irradiating the mammalian skin tissues with a second pulse; emitting the first pulse for a duration of from about 1 femtosecond to about 1 hour; and separating the first pulse from the second pulse by an inter-pulse interval of about 1 microsecond to about 10 seconds. The treatment composition of matter includes a photoreactive substance and is applied in an amount sufficient to cause physiological changes within the mammalian skin tissues upon the mammalian skin being irradiated.

Advantageously, the claimed invention is relatively easy to perform and relatively safe. The claimed invention is furthermore relatively painless when performed in vivo and gives clinically significant results in relatively few treatments.

The invention is relatively well adapted to enhance physiological processes and causes relatively few side effects.

The proposed treatment involves little or no downtime and relatively small or absent tissue damages or inflammation.

In another broad aspect, the invention provides a use of a photoreactive substance in the preparation of a treatment composition of matter for treating mammalian skin tissues, treating the mammalian skin tissues causing a predetermined physiological change in the mammalian skin tissues, wherein the treatment composition of matter is applied onto the mammalian skin tissues, following which: the mammalian skin tissues are irradiated with a first pulse having a power density above an activation threshold power density; the mammalian skin tissues are irradiated with a second pulse; the first pulse is emitted for a duration of from about 1 femtosecond to about 1 hour; and the first pulse is separated from the second pulse by an inter-pulse interval of about 1 microsecond to about 10 seconds; wherein the treatment composition of matter includes a photoreactive substance and is applied in an amount sufficient to cause physiological changes within the mammalian skin tissues upon the mammalian skin being irradiated.

In some embodiments of the invention, the mammalian skin tissues are irradiated with a plurality of pulse trains, each pulse train including at least two pulses. For example, each pulse train includes from 3 to 10 pulses, each pulse has a duration of from about 250 microsecond to about 1 millisecond with an inter-pulse interval of from about 50 microseconds to about 500 microseconds, the pulse trains being separated by a an inter-pulse train interval of from about 500 microseconds to about 2250 microseconds. However, the various parameters mentioned in this paragraph may take alternative values without departing from the scope of the invention.

A technical problem solved at least in part by the claimed invention is the presence of side effects present in prior art PDT methods.

Another technical problem solved at least in part by the claimed invention is the relatively minute influence of non-thermal non-ablative light treatment on the epidermis.

Another technical problem solved at least in part by the claimed invention is the relatively small effects of PDT on the dermis.

Other objects, advantages and features of the present invention will become more apparent upon reading of the following non-restrictive description of preferred embodiments thereof, given by way of example only with reference to the accompanying drawings.

BRIEF DESCRIPTION OF THE DRAWINGS

Embodiments of the present invention will now be disclosed, by way of example, in reference to the following drawings in which.

DETAILED DESCRIPTION

Figure 1A:
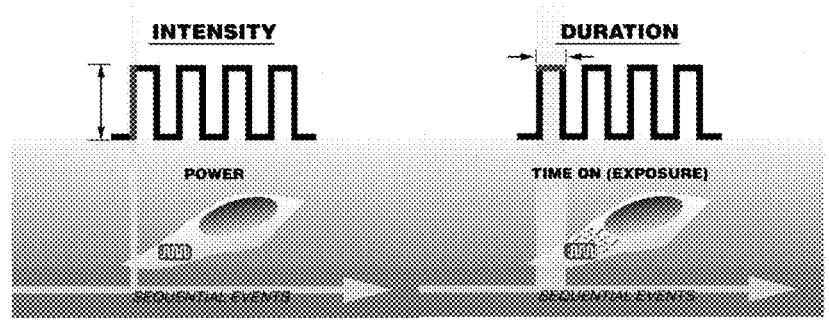
FIGS. 1A to 1D illustrate schematically a sequential pulsing mode that may provide molecular and cellular resting intervals.

The following text proposes a number of mechanisms through which the claimed invention achieves desired effects. However, some embodiments of the invention achieve the desired effect through alternative mechanisms. Accordingly, the proposed mechanisms should not be interpreted to restrict the scope of the appended claims that do not claim such mechanisms.

Photoregulation

Photoregulation involves downregulating or upregulating specific metabolic pathways by light therapy and a treatment composition of matter including a photoreactive substance applied onto mammalian skin tissues. In summary, the invention involves a method for enhancing the epidermis and the dermis of mammalian skin simultaneously reducing possible exogenous and endogenous damage. A treatment composition of matter including a photoreactive substance is topically applied on the epidermis and is photochemically activated by light. For example, and non-limitatively, the light is light emitted by light emitting diodes (LED).

This light also reaches the dermis. Both epidermis and dermis are targeted by this therapeutic strategy involving little or no downtime and relatively quick and efficient results translating in increased skin quality are obtained. The disclosed method reverses at least in part damages associated with keratinocytes/collagen/elastin alterations.

For the purpose of this specification, the following definitions apply. First, the term Photoinduction™ refers to the illumination of mammalian skin tissues with non-thermal pulsed radiation. In one example, the radiation is produced using Light Emitting Diodes (LEDs) which obey a predetermined duty cycle. Of course, should LEDs not necessitating a predetermined duty cycle be used, many constraints regarding the irradiation are removed.

In a specific example of implementation, photoinduction includes irradiating the tissue with radiation defining a plurality of pulse trains, each pulse train including a plurality of radiation pulses. The pulse trains are separated by inter-train time intervals wherein no pulses are produced.

The term pulse is to be broadly interpreted. For example, the pulses need not be of a substantially uniform power density with a substantially total absence of power density within the inter-pulse intervals, even if such pulses are an example of pulses suitable for use in some embodiments of the invention.

Indeed, each pulse may present a time evolution leading to pulses having any suitable time evolution. Also, during the inter-pulse interval, the power density is substantially smaller than a power density within each pulse, but not necessarily zero.

Photoregulation refers to the use of Photoinduction™ on tissues for which the treatment composition of matter including the photoreactive substance has been previously topically applied on the skin and that reaches especially the epidermis.

The term mammalian skin tissue refers both to in vivo mammalian skin, including non-limitatively human skin, and to in vitro mammalian skin tissue cultures.

In examples found hereinbelow, the photoreactive substances used are copper peptides and/or 10% vitamin C in treatment compositions of matter taking the form of creams. However, the reader skilled in the art will readily appreciate that these creams are not the only treatment compositions of matter that are within the scope of the invention as the claimed method can involve other topical agents photochemically activated by the light parameters involved in Photoinduction™ This relatively non-irritating application is relevant for all warm-blooded animals, including in vivo mammalian skin, as well as in vitro tissue.

The method described herein involves the photoreactive substance as well as Photoinduction™ acting in synergy to improve skin texture/integrity. A photoreactive substance included in a treatment composition of matter applied to the epidermis (skin surface) promotes keratinocyte turn-over and provides a relatively silkier/smoother skin while enhancing overall texture, relatively decreasing pore size, repairing at least in part photodamaged skin and reducing hyperpigmentation spots. On the other hand, dermal fibroblast stimulation contributes to enhance collagen production, which results in relatively improved skin resiliency. De novo accumulation of dermal collagen further remodels the dermis, adding to benefits observed on the epidermal section of the skin. Furthermore, dermal collagenase or (collagen degrading enzymes or MMP (metalloproteinase)) are relatively inhibited and elastin metabolism promoted. De novo dermal collagen production and accumulation is associated with reduction in fine lines, wrinkles, skin glow and pore size.

This two-level approach comprises the activation of the photoreactive substance by specific light parameters to promote epidermal renewal combined with dermal Photoinduction™ improving collagen production. A purpose of the claimed invention is to increase epidermal renewal by promoting keratinocytes turn-over (improved surface roughness and epidermal integrity) while promoting dermal fibroblast collagen production (improved resiliency, suppleness and texture). The application of an exogenous photoreactive substance to the epidermis, followed by a light treatment, appears to enhance skin appearance, improving overall skin tone, skin texture and pore size in a non-cytotoxic cytomodulatory manner. The skin would appear more youthful, smoother and silkier.

A proper non thermal light of carefully selected wavelength, dose and pulsing pattern, once delivered, could activate a previously applied photoreactive substance in a different way than the prior art PDT (Photodynamic Therapy) treatment, the topical agent not being a photosensitizer but rather a specially formulated molecule in a topical base such as, non-limitatively relatively short chain amino acids (dermatopeptides), chromophores, chlorophyll derivatives, vitamin derivatives, anti-oxidants and/or any free radical quenchers that may have a positive effect on keratinocyte or extracellular milieu once light is absorbed.

Light absorption by the photoreactive substance brings the molecules of photoreactive substance to higher energy states and induces photoactivation to clinically active metabolites within the epidermis. Moreover, Photoinduction™ simultaneously stimulates dermal fibroblasts to secrete procollagen and basic fibroblast growth factor. This claimed invention relates to a synergy between light and a photoreactive substance stimulating the epidermis and light alone stimulating the dermis simultaneously (dual effect) to promote overall skin renewal.

This document suggests a method with simultaneous synergistic effects of pulsed optical LED energy for the activation of a photoreactive substance triggered by real-time Photoinduction™ of dermal fibroblasts leading to increase gene expression promoting the enhancement of collagen and elastin metabolism. Dermal remodelling and epidermal renewal would both occur using this dual approach. Photoinduction™ increases fibroblast procollagen secretion while reducing metalloproteinase (MMP) or collagenase production. This method involves irradiation with a predetermined number of pulses of non-thermal light, having a predetermined electromagnetic spectrum, a predetermined duration, a predetermined pulse interval, and a predetermined intensity/dose. Minimal or no photothermal damage occurs to the skin during such treatment. Furthermore, Photoinduction™ anti-inflammatory properties modulate photobiological reactions taking place in the epidermis to lower possible irritation/erythema phenomena.

Light propagation in the skin depends on the presence of exogenous or endogenous chromophores. Based on well-known light-tissue interactions, part of incident light is reflected at the surface of the skin. Most incident light penetrates the skin. Once absorbed, light reaches cells and triggers a tissue effect, yet some light might also be transmitted through the skin with or without the generation of a bioresponse. In the claimed invention, LED photons progressively travel through the epidermis where they are absorbed by the photoreactive substance for a specific intended use. Then, some photons are transmitted to the papillary and subsequently the reticular dermis where most will be absorbed by specific targets like dermal fibroblasts, increasing collagen production. In the epidermis: the photoreactive substance is photoactivated. Part of the pulsed light energy is absorbed by the photoreactive substance. Then, reduced epidermal cytotoxic effects and cytomodulatory effects (either enhancing or inhibiting effects) occur and skin appearance is improved depending on the properties of the photoreactive substance: parameters will vary regarding its nature, length, concentration, incubation, absorption coefficient in the tissue and light source parameters (wavelength, intensity and dosage). Simultaneous transmittance of unabsorbed pulsed light energy also takes place throughout the epidermis, until it is finally absorbed within the dermis by papillary and subsequently reticular dermis (especially by fibroblasts). Such a deeply located absorption induces the Photoinduction™ of dermal fibroblast. Signal transduction and amplification seem to also promote complex anti-inflammatory mechanisms able to modulate epidermal and dermal inflammatory reactions. Gene expression profiles in human fibroblast cells irradiated with red light reported direct and indirect activation of pathways related to anti-inflammatory processes (Zhang et al., 2003).

Zhang and collaborators have demonstrated in 2003 though cDNA microarray analysis following red light irradiation, the upregulation of proliferation, DNA repair, anti-oxidant-metabolism-related, genes, and down regulation of genes related to antiapoptosic activity. Light therapy is also thought to increase phagocytosis, angiogenesis, and the release of ATP while stimulating the secretion of endorphins. Downregulation of excessive inflammatory epidermal reaction that might be secondary to the treatment of the epidermis allows for smoother and silkier skin, with reduced risk of redness and skin irritation.

Treatments are relatively or totally painless and ultimately offer better clinical outcomes with both epidermis and dermis stimulated and acting together. This innovative combination treatment lays the mechanistic groundwork for further ongoing studies that attempt to optimize topical absorption in the epidermis, through the modulation of the critical inflammatory mediators.

Pulsed Light Source

Figure 1B:
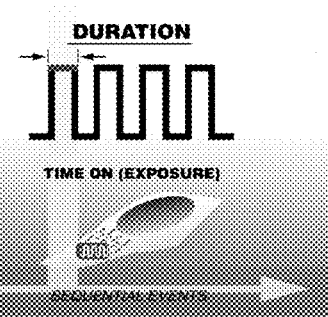
Figure 1C:
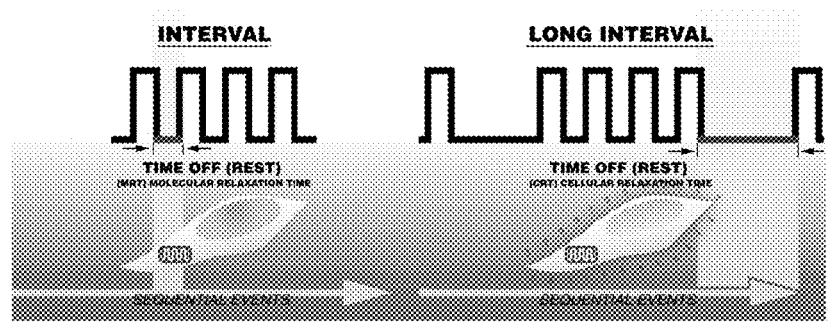
Figure 1D:
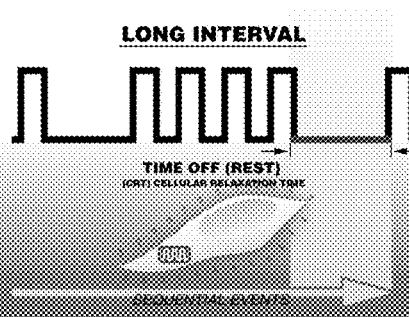

Photoinduction™ using pulsed optical energy should be considered instead of continuous wave optical energy, to avoid possible cellular exhaustion and deliver optimal stimulation (FIGS. 1A to 1D). It is hypothesized that pulsed LED light, when compared to continuous waves (CW), would leave a rest to the fibroblast preventing cell exhaustion (Barolet et al., in preparation). Referring to panel A, the threshold irradiance (mW/cm$^2$) or intensity per unit area must be reached to activate the fibroblast. As shown in FIG. 1B, the exposure duration (time on) is a monitored factor. Referring to FIG. 1C, the pulse interval is allows to control molecular relaxation (time off). With reference to FIG. 1D, a longer downtime between predetermined number of pulses intervals (<10) leading to successive inter-pulse train intervals may provide a resting phase for treated fibroblasts—or cellular relaxation time—assuming that inter-pulse train interval >pulse interval. This alternatively could give the fibroblast more time to secrete type I collagen in the extracellular matrix (ECM). Photoinduction™ and an apparatus for performing Photoinduction™ are described in PCT Patent Application PCT/CA2005/000185 filed Feb. 7, 2005 in the name of Barolet et al.

Once the cellular threshold irradiance is reached, physiological activation will be initiated as light will stimulate cells that grow poorly at the time of irradiation, maximizing cellular proliferation potentials (Karu et al., 1988; 1999; 2004). Karu reports differences, for the same cells, between biological cellular responses to continuous wave (CW) and pulsed light of the same wavelength and dose.

Enhanced Collagen Production by Photoinduction™

Pulsed LED light source reaching the dermis promoted the upregulation of fibroblasts type 1 procollagen while downregulating MMP-1 expression, leading to overall type I collagen deposition and enhanced overall clinical skin appearance. Occurring fragmentation of type 1 collagen by collagenases would act as to promote collagen loss both in aged and photodamaged skin, as the damaged protein would downregulate collagen synthesis by cells naturally able to produce collagen (Varani et al., 2002; Fliegel et al., 2003). The balance between collagen synthesis and degradation is suggested to be different in photodamaged versus naturally aging skin, as sun damaged skin would secrete more MMPs (Chung et al., 2001). However, for both aged and photoaged skins, the end result is a net loss in dermal collagen. We observed that pulsed LED light exposures appear to significantly catalyze resistance to aging/photoaging damages by amplifying type 1 procollagen deposition while decreasing collagenase (MMP-1) activity, which results in a boosted collagen synthesis. Beneficial reversal of aging collagen to collagenase ratio via a pulsed low energy LED light source had not been reported to date as it is for tretinoin topical therapy. From what we observed, in vitro dermal fibroblast procollagen upregulation and MMP downregulation relate to clinically significant in vivo results introducing low energy non-thermal LED therapy as a potent skin rejuvenation strategy. Recently, gene expression profiles of human fibroblasts irradiated by low-intensity red light reported direct and indirect activation of pathways related to cellular proliferation and metabolism, stress and apoptosis mechanisms, as well as DNA repair, along with transcription (Zhang, 2003).

In vitro studies performed in our laboratory demonstrated that exposure to sequentially pulsed non-thermal LED light therapy, thoroughly performed and using the appropriate combination of parameters, upregulates fibroblast type 1 procollagen synthesis, while collagenase (MMP-1) production is down-regulated following a proportional trend. In vivo analysis we conducted correlated these findings with corresponding rhytid and skin surface characteristic microtopographic improvements in the majority of patients. This study adds evidence to the contribution of low energy light therapy in the regulation of dermal collagen metabolism, emphasizing LED technology as a promising non-thermal, non-ablative skin rejuvenation strategy.

Photoreactive Substance

The photoreactive substance absorbs light energy and non-thermal radiation. The treatment composition of matter applied to the skin and photoactivated can include in a non-limitative manner:

1. active ingredients including at least one metal bond, wherein the active ingredient in the metal-bond is selected from the group consisting of Fe, Mg, Cu, Al reactive transitions metals, metal chelates and antibody complexes;
2. dermatopeptides (polypeptides between about 3 and about 60 amino acids in length) having anti-aging activity, ceramide providing improvement in anti-aging activity of polypeptide and additional topicals to improve skin appearance and tone and support wound healing;
3. vitamin C;
4. collagen or elastin related peptides;
5. chlorophyll derivatives;
6. other chromophores;

7. other peptides; and
8. other topicals.

At least some useful photoreactive substances are such that exposure to light within the absorption spectrum of the photoreactive substance does not lead to fluorescence emission. These photoreactive substances or their photoproducts would be preferentially absorbed especially but not limitative to the epidermis, or trigger a reaction involving the epidermis.

Light activation of photoreactive substance allows photobleaching and increased formation of photoproduct/active metabolite capable of inducing renewal of epidermal keratinocytes and cellular elements of the upper dermis.

The following examples of treatment were performed with copper peptide and 10% vitamin C creams, but such examples are non-limitative and it is within the scope of the invention to use any other photoreactive substances.

EXAMPLES

In Vitro Experiments

In Vitro Experiments: Human Reconstructed Skin Model
  Cell Culture Media.
  Keratinocytes were grown in complete DME-HAM medium: a combination of Dulbecco-Vogt modification of Eagle's medium (DME) with Ham's F12 in a 3:1 proportion (Gibco), supplemented with 5% Fetal Clone II serum (FC-SII) (HyClone, Logan, United States), 10 ng/mL epidermal growth factor (Austral biologicals, San Ramon, United States), 24.3 µg/mL adenin (Sigma), 5 µg/mL insulin (Sigma), 5 µg/mL transferrin (Roche), $2 \times 10^{-9}$ M 3,3' 5' triiodo-L-thyronin (Sigma), 0.4 µg/mL hydrocortisone (Calbiochem, La Jolla, United States), 100 IU/mL penicillin G (Sigma), and 25 µg/mL gentamycin (Schering, Pointe-Claire, Canada). Fibroblasts were cultured in DME containing 10% fetal calf serum (FCS) (HyClone), 100 IU/mL penicillin G, and 25 µg/mL gentamycin.
  Cell Isolation.
  Human epidermal keratinocytes and dermal fibroblasts were isolated from normal skin specimens; keratinocytes are mainly found in the epidermis while fibroblasts are localized in the dermis. Skin specimens were collected from a healthy adult female aged 38 years old during reductive breast surgery (F38). Procedures for cell isolation were initiated within three hours following the surgery according to previously published methods (Germain et al., 2001; Auger et al., 2002).
  Cream.
  Prior each of the eleven (11) LED treatment, a copper peptide cream (Neutrogena—Visibly Firm™) was carefully applied with a sterile Q-Tips™ on the epidermis (top layer) of the human reconstructed skin. Extra concern was provided to minimize damages to the human reconstructed skin in vitro samples during this procedure.
  Light Source.
  The various light sources tested were supplied by OPUSMED inc. and were gas sterilized prior to handling in the tissue culture laboratory. Herein, one low energy LED light sources (wavelength 660 nm) and three different sequential pulsing modes were investigated (Table 1). During the course of this experiment, treatment distance for both in vitro and in vivo testing was maintained at 2.5 cm. Total fluence and power density were respectively kept steady at 4 J/cm$^2$ and 50 mW/cm$^2$, in order to analyse the influence of wavelength and pulsing mode. Light intensity or irradiance was delivered to the skin for 160 seconds, including various time on and time off sequences (pulsing pattern).

TABLE 1

LED Light pulsing modes. During the course of this experiment, three light pulsing modes were tested. For each mode, key parameters combined altogether composed a specific pulsing pattern.

| TESTED PARAMETERS | Mode A | Mode B | Mode C |
|---|---|---|---|
| Pulsewidth (time on) (µsec) | 500 | 500 | 500 |
| Pulse Interval (time off) (µsec) | 150 | 100 | 50 |
| # Pulse per Pulse Train (number of pulse) | 4 | 4 | 4 |
| Pulse Train Interval (µsec) | 1550 | 1700 | 1850 |
| Irradiance (mW/cm$^2$) | 50 | 50 | 50 |
| Total Treatment Time (sec) | 160 | 160 | 160 |

In Vitro Photoinduction™ of Human Reconstructed Skin (HRS).

A complete biological human reconstructed skin was produced as described in Laplante et al., 2001. HRS cultures were exposed to LED light under a laminar flow hood. Prior to LED light exposure, Petri dish covers were removed. Each culture plate was then placed so that the 2.5 cm distance between the reconstructed skin and the light source was respected. Reconstructed skin specimens were then irradiated with the selected LED light source with the predetermined pulsing mode. HRS were incubated at 37° C. (8% CO2). Cells were treated 4 times with two (2) biweekly treatments. Previous LED light only experiments had shown that healthy HRS could easily be kept for over a month in culture, however in that case the mechanical application of a cream prior to each LED light was found to damage the HRS top section, critically impacting on testing and results. However, six (6) treatments were suitable for the samples and tests were respectively performed in triplicate, for the following four (4) groups: 1. Q-tip only, 2. cream only, 3. light only, and 4. cream and light. Culture medium was collected prior to each treatment and after the last treatment, then stored at −20° C. until assessed for type I procollagen and MMP-1. New medium was added after every LED exposure.

Type I Collagen and MMP-1 Determination.

Human type I collagen was measured in cell culture supernatants of the selected time period with the Protype I collagen C-peptide enzyme immunoassay (EIA) kit purchased from Takara Mirus Bio (Madison, Wis., USA). Human type I procollagen is synthesized as a precursor molecule called procollagen type I collagen that contains additional peptide sequences, usually called propeptides. These propeptides are cleaved off from a collagen triple helix molecule during their secretion, after which triple helix collagen polymerizes into new extracellular collagen fibrils. Thus, the amount of free propeptides reflects stoichiometrically the total product of type I collagen molecules synthesized. Total (latent plus active form) and active (substrate degrading enzyme only) levels of MMP-1 were also measured using the MMP-1 biotrak activity assay systems according to the manufacturer procedures (Amersham Biosciences, Baie D'Urfé, Québec, Canada). The culture medium used for our experiments was not found to interfere with any of the assays used for the dilutions of supernatant used for the dosage. This experiment has been done using three different HRS and each test point was done in triplicate.

Histological Analysis.

Figure 2:
FIG. 2 illustrates a Masson stain of reconstructed skin section (F38 HRS), underlining the presence of dermal collagen in the basal section (dark grey). Keratinocytes found in the epidermis and dermal fibroblasts appear in light grey.

Biopsies of untreated and treated reconstructed skins were fixed at least 24 hours in a Bouin solution (ACP, Canada) and embedded in paraffin. Five mm thick cross-sections were stained with Masson's trichrome (FIG. 2).

Indirect Immunofluorescence Microscopy.

Figure 3:
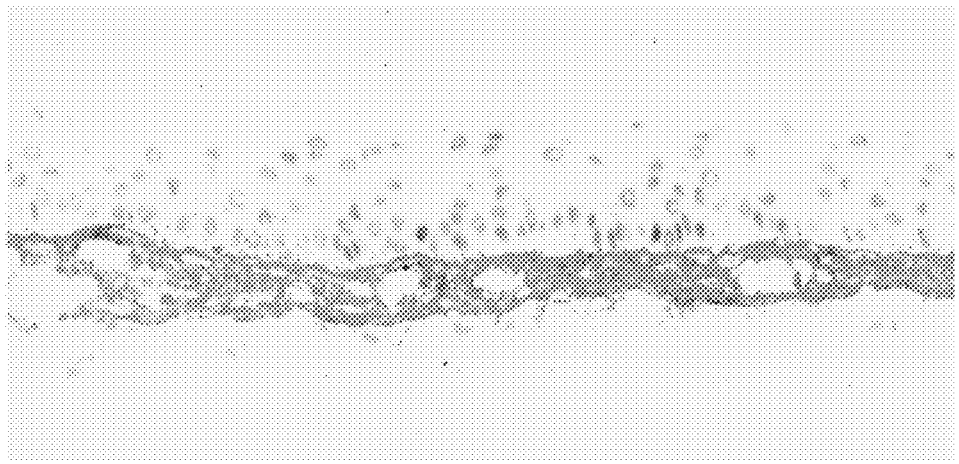
FIG. 3 illustrates a fluorescent immunostaining of an HRS emphasizing increased type I procollagen located in the dermal section (band pattern) after 11 Pulsed LED treatments. Nuclei are stained for both keratinocytes (round nuclei) and dermal fibroblasts (elongated nuclei).

Samples of the untreated and treated reconstructed skin were also embedded and frozen in OCT compound (Somagen, Edmonton, Canada). A four mm thick cross-section of the reconstructed skins were fixed in cold acetone and further incubated with mouse monoclonal anti-human collagen I antibody (Chemicon), and rabbit polyclonal anti-human collagen III antibody (Cederlane), and rabbit polyclonal anti-human elastin antibody (FIG. 3). The secondary antibodies (Chemicon) used were rhodamine conjugated goat anti-mouse IgG-IgM and goat anti-rabbit IgG. Nuclei were stained blue with Hoechst 33258 (Sigma).

In Vitro Results and Discussion:

Normal HRS were grown using one fibroblast primary cell line F38 and a common primary keratinocyte cell line as previously described and respectively identified as HRS F38. HRS were then exposed to 660 nm pulsed light source (Mode A, B, C). Treatments were performed 3 times a week for 2 consecutives weeks (total of 6 treatments). Experiments were performed in triplicate.

FIG. 2 shows both epidermis and dermis section of a HRS F38 emphasizing Masson's Trichrome stain with collagen in dark grey while keratinocytes/fibroblasts appear in light grey. Indirect immunofluorescence microscopy was also performed, as seen in FIG. 3 for an HRS where type I procollagen located in the dermal section appears as a band pattern.

Human reconstructed skins (HRS) were treated with both 660 nm pulsed LED light and a topical cream applied right before light exposure. HRS improvement was measured with dosage of MMP-1, MMP-2 and type I procollagen dermal production. Measurements of type I procollagen or MMP-1 or -2 give indications on collagen/elastin metabolism, without characterizing much the in vitro epidermal part of the HRS. The application of a topical cream on the HRS model required extensive care not to damage the samples.

Results obtained on HRS using mode A are summarized in Table 2. It should be noted that results obtained with modes B and C are not presented because samples used to obtain these results were damaged during the course of the experiment. A slight increase in type I procollagen was observed for the first two (2) treatments, when compared to controls, but improvements were not maintained following those 2 treatments combining both topical and light, while treatment performed with light alone showed a marked increase in type I procollagen production. Repetitive applications of the topical on the top layer of the HRS are thought to have contributed to reduce light propagation in theses reconstructed skin samples. Moreover, since the topical used during this in vitro study was not fully transparent, but rather of an opaque light blue shade and therefore potentially limiting, at various extents, light transmission in the HRS, the simultaneous effect of the topical and the light may have been prevented.

TABLE 2

Human reconstructed skins (HRS) were treated with 660 nm pulsed (mode A) LED light, with or without a topical cream applied right before light exposure. HRS improvement was measured with dosage of MMP-1, MMP-2 and type I procollagen dermal production. Controls involved mechanical rubbing of a Q-Tip on the HRS and treatment of the samples with the cream only, no light being involved.

F38 HRS (six treatments)

| TREATMENT | 1 | 2 | 3 | 4 | 5 | 6 |
|---|---|---|---|---|---|---|
| Procoll (ng/ml) | | | | | | |
| Q-Tip A | 2156 | 3110 | 3606 | 3141 | 4245 | 6785 |
| Cream A | 2944 | 2309 | 3968 | 3092 | 5610 | 6194 |
| 660 mode 1A | 4090 | 3486 | 4869 | 4352 | 6730 | 8496 |
| Cream 660 1A | 4481 | 3180 | 3449 | 3058 | 3846 | 7536 |
| Control A | 2573 | 2542 | 4921 | 3678 | 5016 | 7662 |
| MMP-1 Active (ng/ml) | | | | | | |
| Q-Tip A | 2.1 | 1.7 | 3.1 | 2.3 | 1.4 | 2 |
| Cream A | 3.2 | 2 | 2 | 5.8 | 3.9 | 4.8 |
| 660 mode 1A | 2.1 | 1.7 | 2.3 | 3.2 | 2 | 3.1 |
| Cream 660 1A | 3.7 | 3.6 | 2.6 | 3.2 | 2.2 | 3.2 |
| Control A | 2.1 | 2.3 | 2.5 | 2.9 | 2.6 | 3.7 |
| MMP-1 Total (ng/ml) | | | | | | |
| Q-Tip A | 43.5 | 30.7 | 41.4 | 39.1 | 27 | 37.2 |
| Cream A | 68.8 | 60.1 | 71.9 | 87.9 | 54.4 | 94.8 |
| 660 mode 1A | 40.2 | 31 | 45 | 27.8 | 37.1 | 43.5 |
| Cream 660 1A | 65.4 | 65.4 | 54.7 | 55.9 | 63.6 | 65.3 |
| Control A | 37.3 | 32.4 | 42.9 | 41.3 | 44.4 | 40.4 |
| MMP-2 Total (ng/ml) | | | | | | |
| Q-Tip A | 122 | 120 | 101 | 110 | 146 | 126 |
| Cream A | 153 | 144 | 135 | 122 | 116 | 125 |
| 660 mode 1A | 102 | 104 | 106 | 117 | 100 | 108 |
| Cream 660 1A | 133 | 122 | 143 | 117 | 135 | 123 |
| Control A | 123 | 117 | 93 | 129 | 122 | 114 |

On the other hand, while MMP1- and MMP-2 productions were found to be significantly lowered by light alone, reductions were only slightly lowered when a topical and light were used together. But again, repetitive applications of the topical on top of the HRS could have considerably lowered light propagation in the dermis, and therefore any physiological response.

In Vivo Experiments:

Case Reports

Participants (Fitzpatrick phototypes I to III) were treated following the therapeutic strategy established by a medical doctor with a LED device (LumiPhase-R™, OPUSMED inc. Montreal, CANADA) on a half-face (split face study). A topical copper peptide cream (CPC) (Visibly Firm™ (Neutrogena)) or 10% vitamin C (Active C™ (La Roche-Posay)) was applied topically immediately prior each LED treatment on a first half-face, while the other half-face was irradiated without application of the topical cream. Treatments were performed with no cooling method and delivered sequentially pulsed LED treatments in 160 seconds, with a total fluence of 4 $J/cm^2$. During the course of this experiment, treatment distance was maintained at 2.5 cm from the treated area. Power density was kept steady at 50 $mW/cm^2$. The treatments were delivered at 660 nm light in pulsed mode described herein as Mode A.

Patient 1 (Photodamage)

A 46 years-old female underwent six (6) LED treatments on her face. A copper peptide cream (CPC) was applied on right half-face. The topical cream was applied before treatment and promoted enhancement in skin texture while reducing pore size on the right half-face relative to the left half-face. Photodamage was reduced following LED therapy used alone, but significant clinical improvement were observed on the side treated with both CPC and LED therapy. Added enhancement in fine lines, pore size and dyspigmentation were noticeable. No pain or redness (erythema) was related to the application of the CPC prior to LED treatment.

Patient 2 (Wrinkle Reduction)

A 42 years-old male received ten (10) biweekly treatments where a CPC was applied to the right half of his face prior to each LED exposure. The right half-face (CPC and light) exhibited better skin tone and texture mostly around the periorbital area relative to the left half-face. Periorbital fines lines were reduced and skin appeared more opaque (increased skin surface reflectivity). No burning sensation or erythema was reported during and post-treatment.

Patient 3 (Hyperpigmentation)

A 48 years-old woman was treated for facial hyperpigmentation (melasma) with eight LED treatments. A 10% vitamin C cream was applied on the left half-face prior to each LED exposure. Hyperpigmentation gradually decreased to homogenous demarcation and then mostly vanished away. Benefits obtained up to 2 weeks after the last treatment showed further enhancement on the vitamin C treated side. No erythema was observed.

Patient 4 (Favre Racouchot)

A 45 years-old woman was treated for Favre Racouchot lesions in the malar area (dermatoheliosis with multiple milia). She had previously undergone $CO_2$ laser resurfacing and exhibited post-$CO_2$ hyperpigmentation. She was treated with three LED treatments, with the left half-face combined with pre-treatment application of 10% vitamin C. The hyperpigmentation significantly decreased on the left side where topical vitamin C had been applied as compared to the right side.

Patient 5 (Apocrine Hydrocystoma)

A 57 years-old man was treated for apocrine hydrorcystoma of the lower eyelids. In 1996 he had previously undergone two copper vapor laser treatments and one YAG (Q-switched) laser treatment. In 1998, he received his first $CO_2$ laser treatment, and two additional treatments were performed in 1999 and one in 2000. To further enhance results already seen with $CO_2$ laser, this patient was treated in 2003 with 6 LED treatments, followed by four other treatments in 2004. Those last 4 LED treatments were performed with CPC applied pre-treatment on the left half-face. A month later, significant clinical improvements were seen on the side treated simultaneously with the topical agent enhancing LED therapy. No irritation was observed.

Patient 6 (Wrinkles)

A 49 years-old woman consulted for periorbital wrinkles. Overall, she received 12 LED treatments and prior to each treatment, CPC had been applied to the right half face. At follow-up, the right side exhibited better texture, improvement in fine lines and dyspigmentation relative to the left side. No erythema was noticed during treatment. Benefits were found to reach their maximum one month post-treatment.

Treatment Composition of Matter and Photoreactive Substance

The treatment composition of matter includes the photoreactive substance and, in come embodiments of the invention, a substrate. When present, the substrate allows an adjustment of the concentration of the photoreactive substance to achieve desired results. Also, the substrate helps in spreading the photoreactive substance over the skin surface.

Examples of photoreactive substances have been given hereinabove. In some embodiments of the invention, suitable photoreactive substances are of a pH of from about 6 to about 8 and are stable at room temperature. The substrate is any suitable liquid, lotion of cream, which may or may not have a non-zero Sun Protection Factor (SPF).

Many conditions may be treated using the claimed invention. A non-exhaustive list of such conditions is:

a. cutaneous textural changes induced by aging, photodamage and atrophic acne, and mild erythema;
b. dyspigmentation (lesions/diseases) of the skin;
c. hyperkeratotic lesions/diseases of the skin;
d. inflammatory lesions/diseases of the skin, such as non-limitatively psoriasis, eczema and dermatitis;
e. neoplastic & pre neoplastic diseases of the skin, such as for example actinic keratoses;
f. granulomatous diseases of the skin, such as for example sarcoidoisis; and
g. infectious diseases of the skin, such as for example impetigo.

It is hypothesized that photoregulation alters immune system reactions in the skin (effects on cell turnover and the skin's immune response). It may also reduce synthesis of DNA within epidermal cells if keratinocyte turnover is too fast and conversely if too slow. Another possible mechanism is the interaction of the chromophore photoproduct into keratinocyte DNA forming cross links as in PUVA therapy. For example, copper (Cu) seems to promote better skin renewal, which may be due to the fact that copper is a cofactor in protein synthesis, as for example in collagen synthesis. The kinetics of photoregulation depends on chromophore formulation.

In some embodiments of the invention, the mammalian skin tissues are irradiated immediately after the application of the treatment composition of matter. In alternative embodiments of the invention, there is an incubation period of from about 1 second to about 24 hours, among others, between the application of the treatment composition of matter and the beginning of the irradiation. In this case, in some embodiments of the invention an occlusion (with adhesive or non adhesive membrane or dressing) is used to prevent evaporation of the treatment composition of matter. However, in alternative embodiments of the invention, no occlusion is used.

Interactions between mammalian skin tissues and a topical agents are further detailed in the following documents: Thornber, 1975; Sportelli et al., 1977; Kaizer and Kezdy, 1987; Lau et al., 1989; Elrad et al., 2002; Chiu and Kimball, 2003; Achilefu et al., 2005.

Figure 4:
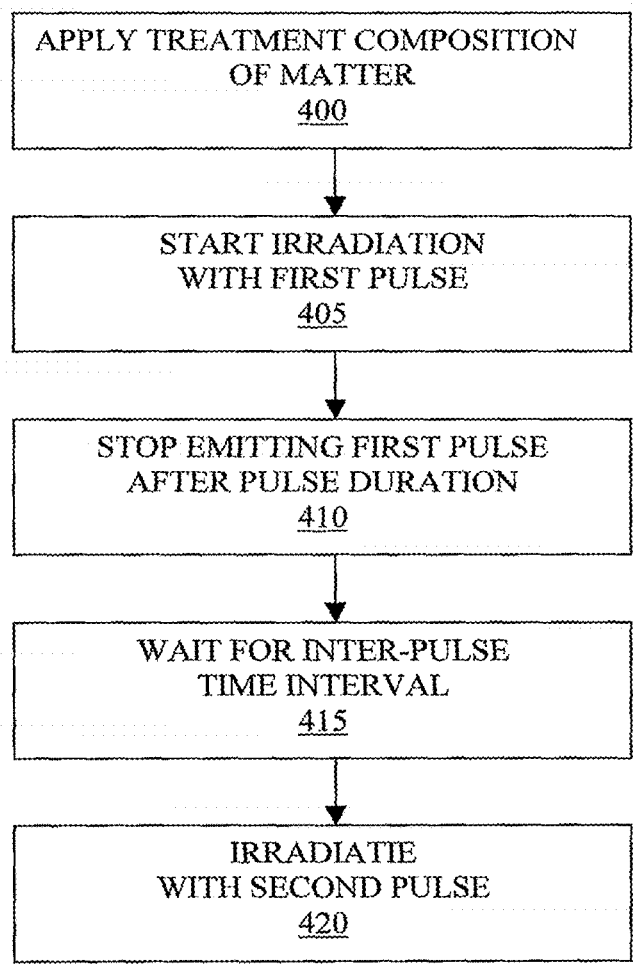
FIG. 4, in a flowchart, illustrates a method for treating mammalian skin tissues in accordance with an embodiment of the present invention.

Referring to FIG. 4, a method of treating mammalian skin tissues for causing a predetermined physiological change in the mammalian skin tissues is illustrated. The method includes applying onto the mammalian skin tissues a treatment composition of matter including a photoreactive substance (step 400).

Thereafter, the tissue is irradiated with a first pulse having a power density above an activation threshold power density (step 405). The activation threshold power density is a power density below which the predetermined physiological change is substantially absent from the mammalian skin tissues upon the mammalian skin tissues being irradiated with the radiation and above which the predetermined physiological change is substantially present in the mammalian skin tissues upon the mammalian skin tissues being irradiated with the radiation.

The first pulse is emitted for a pulse duration of from about 1 femtosecond to about 1 hour (step 410). The first pulse is separated from a second pulse by an inter-pulse interval of from about 1 microsecond to about 10 seconds (step 415). The mammalian skin tissues are then irradiated with a second pulse (step 420).

Typically, the first and second pulses have a wavelength of from about 400 nanometers to about 1500 nanometers and a power density of about 0.1 mW/cm$^2$ to about 10 W/cm$^2$, and in some embodiments of the invention of from about 30 mW/cm$^2$ to about 100 mW/cm$^2$.

In further embodiments, the activation threshold power density can be about 0.1 mW/cm$^2$, about 10 mW/cm$^2$, and/or about 50 mW/cm$^2$. The inter-pulse interval can be about 10 microseconds to about 5 milliseconds or about 100 microseconds to about 0.5 milliseconds. Duration of the first and subsequent pulses can be about 100 microseconds to about 5 milliseconds or about 250 microseconds to about 1 millisecond. Typically, all the pulses are emitted by at least one light emitting diode (LED). Another embodiment includes the step of emitting the first pulse for about 250 microseconds to about 1 millisecond with the inter-pulse interval from about 100 microseconds to about 0.5 millisecond.

The physiological effect of the claimed method can include at least one of stimulating collagen production by fibroblasts contained within the mammalian skin tissues and modulating an apoptosis response of the mammalian skin tissues. Further physiological effects have been described hereinabove.

Some embodiments utilize ratios of key factors, including a ratio of the duration divided by the inter-pulse interval that can be about 0.1 to about 10 and about 0.5 to about 2. In another embodiment, the power density of radiation within the tissue is below one of about 10 percent and about 1 percent of the activation threshold power density during the inter-pulse interval.

Furthermore, a minimal power density of the radiation within the tissue during each pulse can be about two times, about ten times, about 100 times, or about 10,000 times as large as a maximal power density of the radiation within the tissue during the inter-pulse interval.

Another method of photoactivation includes the steps of irradiating the tissue with a first pulse having a power density below a thermal threshold power density. The thermal threshold power density is a value over which a temperature of the irradiated tissue increases to a temperature greater than a predetermined overheating temperature. The thermal threshold power density can be about 10 mW/cm$^2$, about 100 mW/cm$^2$, about 1 W/cm$^2$, and about 1 kW/cm$^2$. The overheating temperature can be about 2° C., about 0.5° C., and about 0.1° C. over a maximal non-pathological in-vivo temperature of the mammalian tissue. Further, the activation threshold power density is about 30 mW/cm$^2$ and the thermal threshold power density is about 100 mW/cm$^2$.

Figure 5:
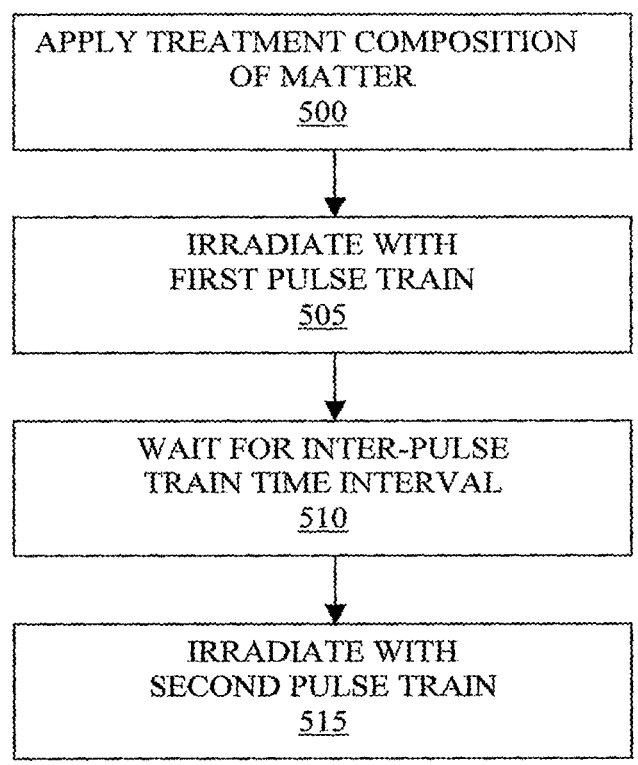
FIG. 5, in a flowchart, illustrates a method for treating mammalian skin tissues in accordance with an alternative embodiment of the present invention.

FIG. 5 illustrates a method wherein at least two pulse trains are utilized. Each pulse train includes a first pulse and a second pulse. The method includes applying onto mammalian skin tissues a treatment composition of matter including a photoreactive substance (step 500) and emitting a first pulse train (step 505). The first pulse train is separated from the second pulse train by an inter-pulse train interval of about 1 microsecond to about 1 second (step 510) and the second pulse train is then emitted (step 515). The inter-pulse train interval is one of 500 microseconds to about 1 second, about 750 microseconds to about 2,250 microseconds, and about 500 microseconds to about 2.25 milliseconds. A number of pulses emitted within each pulse train can be 2 to 100 pulses, 4 to 10 pulses, and 3 to 10 pulses, all of which are within the duty cycle of the light source, specifically the LED.

Figure 6:
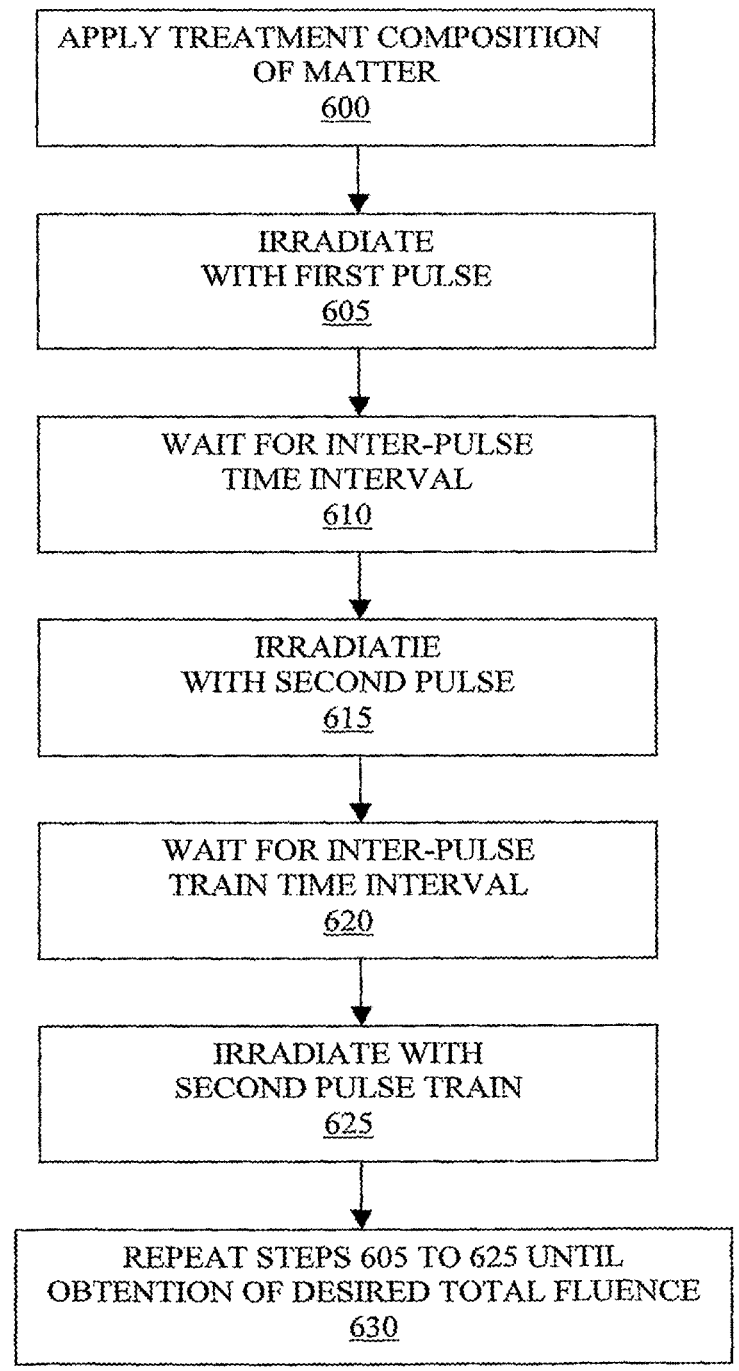
FIG. 6, in a flowchart, illustrates a method for treating mammalian skin tissues in accordance with another alternative embodiment of the present invention.

Another method of photoactivating mammalian tissue causing a predetermined physiological change is illustrated in FIG. 6. Further to the application onto mammalian skin tissues a treatment composition of matter including a photoreactive substance (step 600), the tissue can be irradiated with a first pulse train (steps 605 to 615) and a second pulse train (step 625), each pulse train having at a first pulse (step 605) and a second pulse (step 615). The first pulse can be separated from the second pulse by an inter-pulse interval (step 605) and the first pulse train can be separated from a second pulse train by an inter-pulse train interval (step 620). In some embodiments, the inter-pulse train interval can be about 1 microsecond to about 1 second, 500 microseconds to about 1 second, about 750 microseconds to about 2,250 microseconds, or about 500 microseconds to about 2.25 milliseconds. Further, a ratio of the inter-pulse train interval to the inter-pulse interval is about 2 to about 10, and specifically the ratio of the inter-train pulse interval to the inter-pulse interval is about 3. Other embodiment include a number of pulses within each pulse train is one of 2 to 100 pulses, 4 to 10 pulses, and 3 to 10 pulses.

Other steps include depositing a total fluence from the first and second pulse trains to the tissue of about 0.001 J/cm$^2$ to about 20,000 J/cm$^2$ (step 625). Alternately, the total fluence can be about 4 J/cm$^2$ to about 10 J/cm$^2$ and may be deposited using more than 2 pulse trains.

In addition to activating the photoreactive substance, the invention relates to a method of photoactivating mammalian tissue causing a predetermined physiological change. In this method, irradiating the tissue with a time-varying radiation including a power density temporal profile. The irradiating step can include activating molecular cascades of events and activating cells contained within the tissue. A molecular relaxation phase can be provided and includes additional methods. Molecular relaxation can be allowed wherein a reversible molecular conformational changes are reversed at least in part so that the molecular cascades of events are reactivatable and allowing the cells of the tissue to rest so as to prevent at least in part cell exhaustion during the irradiation.

Further embodiments include preventing a temperature increase in the tissue above an overheating temperature at which the cascade of events triggered by the radiation are substantially reversed. A thermal relaxation phase can be provided that includes allowing the cells of the tissue to dissipate heat so as to remain substantially below the overheating temperature (the tissue remains at a physiological temperature). Further, temperature increases can be prevented by one or more methods, including by a thermal inertia of the tissue, cooling the tissue which can include active convective cooling and delivering to the tissue a vasodilatator in an amount effective to cause a vasodilatation within the tissue.

Some embodiments include power density temporal profiles remaining below a thermal threshold above which the temperature within the tissue is likely to increase above the overheating temperature. Additionally, the molecular cascade of events can be initiated by receiving, by an antenna molecule, at least one photon contained within the radiation. Further, the molecular cascade of events occurs partly in the mitochondria of the cells of the tissue and include reversible conformational changes that are reversed during the molecular relaxation phases. Activating the cells can also include progressively increasing a mitochondrial activity level within the cells of the tissue.

In embodiments of the invention wherein the tissue is irradiated with a plurality of pulse trains, the plurality of pulses within each pulse train a configured to include a number of pulses to bring the cells to a suitable level of activation. Alternately, or in addition, the number of pulses within each pulse train can be a number preventing the cells from substantially reaching a steady state of activation (for example 4 to 10 pulses). The inter-train interval can provide cellular relaxation phases and allows the cells of the tissue to rest so as to prevent at least in part at least one of cell exhaustion and mitochondrial exhaustion during the irradiation. Specifically, an example of an inter-train interval is about 750 microseconds and about 2,250 microseconds.

In some embodiments of the invention, pulse trains are applied through treatments and the inventive method as claimed includes irradiating the tissue in a plurality of treatment, wherein a treatment includes one or more pulse trains, and providing an inter-treatment time interval between treatments.

In specific embodiments, the inter-treatment time interval is one of about 1 minute to about 1 year, about 1 hour to about 1 month, about 1 day to about 1 week, and about 3 days to about 4 days.

The method includes at least one of 2 to 1000 treatments, 2 to 50 treatments, 5 to 20 treatments, and 12 treatments. Non-limitatively, treatments are provided at a frequency of from 1 to 2 treatments/week. In some embodiments of the invention, maintenance treatments are performed at specific time intervals if needed.

Referring to FIG. 1, D, there is shown an example of a specific pulse train separated from pulses belonging to other pulse trains emitted before and after the specific pulse train. The term "time off long interval" corresponds to the inter-pulse train interval. The time between the pulses of each pulse train, namely the inter-pulse interval is the time off interval, as shown in FIG. 1C. FIG. 1B illustrates the pulse duration.

Although the present invention has been described hereinabove by way of preferred embodiments thereof, it can be modified, without departing from the spirit and nature of the subject invention as defined in the appended claims.

REFERENCES

Achilefu S, Bloch S, Markiewicz M A, Zhong T, Ye Y, Dorshow R B, Chance B, Liang K. Synergistic effects of light-emitting probes and peptides for targeting and monitoring integrin expression. Proc Natl Acad Sci USA. 2005 May 31; 102(22):7976-81.

Almeida-Lopes L, Rigau J, Zangaro R A, Guidugli-Neto J, Jaeger M M. Comparison of the low level laser therapy effects on cultured human gingival fibroblasts proliferation using different irradiance and same fluence. Lasers Surg Med. 2001; 29(2)179-84.

Anderson R R, Parrish J A. The optics of human skin. J Invest Dermatol. 1981 July; 77(1):13-9.

Auger F A, Remy-Zolghadri M, Grenier G, Germain L. "A truly New Approach For Tissue Engineering: The LOEX Self-Assembly Technique". In: Stem cell transplantation and tissue engineering, A. Haverich, H. Graf, eds, Springer-Verlag, Berlin. 2002 Chapter 6:73-88.

Barolet D, Boucher A, Bjerring P. In vivo human dermal collagen production following LED-based therapy: The importance of treatment parameters. 25th Anniversary Meeting of the American Society for Laser Medicine and Surgery, March 30-Apr. 3, 2005. Poster session (259).

Basford J R. Low-energy laser treatment of pain and wounds: hype, hope, or hokum? Mayo Clin Proc. 1986 August; 61(8):671-5. Review.

Bihari I, Mester A. The biostimulative effect of low level laser therapy of long-standing crural ulcer using Helium Neon laser, Helium Neon plus infrared lasers and noncoherent light: Preliminary report of a randomized double blind comparative study. Laser Therapy. 1989; 1(2): 97.

Bjerring P, Clement M, Heickendorff L, Lybecker H, Kiernan M. Dermal collagen production following irradiation by dye laser and broadband light source. J Cosmet Laser Ther. 2002 June; 4(2):39-43.

Bosatra M, Jucci A, Olliaro P, Quacci D, Sacchi S. In vitro fibroblast and dermis fibroblast activation by laser irradiation at low energy. An electron microscopic study. Dermatologica. 1984; 168(4):157-62.

Chiu A, Kimball A B. Topical vitamins, minerals and botanical ingredients as modulators of environmental and chronological skin damage. Br J Dermatol. 2003 October; 149(4):681-91. Review.

Chung J H, Seo J Y, Choi H R, Lee M K, Youn C S, Rhie G, Cho K H, Kim K H, Park K C Eun H C. Modulation of skin collagen metabolism in aged and photoaged human skin in vivo. J Invest Dermatol. 2001 November; 117(5):1218-24.

Conlan M J, Rapley J W and Cobb C M. Biostimulation of Wound Healing by Low-Energy Laser Irradiation, J Clin Periodont (1996) 23, 492-496.

Elrad D, Niyogi K K, Grossman A R. A major light-harvesting polypeptide of photosystem II functions in thermal dissipation. Plant Cell. 2002 August; 14(8):1801-16.

Fligiel S E, Varani J, Datta S C, Kang S, Fisher G J, Voorhees J J. Separation of retinoid-induced epidermal and dermal thickening from skin irritation. J Invest Dermatol. 2003 May; 120(5):842-8.

Germain L, Moulin V, Berthod F, Lopez C A, Goulet F, Auger F A.: "Multiple applications of tissue-engineered human skin". In: Cultured human keratinocytes and tissue engineered skin substitutes R. E. Horch, A. M. Munster, B. M. Achauer, eds. Georg Thieme Verlag, Stuttgart, Germany. 2001: 91-98.

Kaiser E T, Kezdy F J. Peptides with affinity for membranes. Annu Rev Biophys Biophys Chem. 1987; 16:561-81. Review.

Karu T I, Pyatibrat L V, Kalendo G S. Photobiological modulation of cell attachment via cytochrome c oxidase. Photochem Photobiol Sci. 2004 February; 3(2):211-6.

Karu T. Primary and secondary mechanisms of action of visible to near-IR radiation on cells. J Photochem Photobiol B. 1999 March; 49(1):1-17. Review.

Karu, T I. Molecular mechanism of the therapeutic effect of low-intensity laser radiation. Lasers in Life Science 1988; 2, 53-74.

Laplante A F, Germain L, Auger F A, Moulin V. Mechanisms of wound reepithelialization: hints from a tissue-engineered reconstructed skin to long-standing questions. FASEB J. 2001 November; 15(13):2377-89.

Lau S J, Laussac J P, Sarkar B. Synthesis and copper(II)-binding properties of the N-terminal peptide of human alpha-fetoprotein. Biochem J. 1989 Feb. 1; 257(3):745-50.

Moody B R, McCarthy J E, Hruza G J. Collagen remodeling after 585-nm pulsed dye laser irradiation: an ultrasonographic analysis. Dermatol Surg. 2003 October; 29(10): 997-9; discussion 999-1000.

Schindl A, Schindl M, Pernerstorfer-Schon H, Schindl L. Low-intensity laser therapy: a review. J Invest Med. 2000; 48:312-326.

Sommer A P, Pinheiro A L, Mester A R, Franke R P, Whelan H T. Biostimulatory windows in low-intensity laser activation: lasers, scanners, and NASA's light-emitting diode array system. J Clin Laser Med. Surg. 2001 February; 19(1):29-33.

Smith K C. Photobiology and photomedicine: the future is bright. J Invest Dermatol. 1981 July; 77(1):2-7.

Sportelli L, Neubacher H, Lohmann W. ESR an optical absorption studies on the copper (II) interaction with small peptides containing aromatic amino acids. Biophys Struct Mech. 1977 Sep. 28; 3(3-4):317-26.

Thornber J P. Chlorophyll-Proteins: Light-Harvesting and Reaction Center Components of Plants. Ann Rev of Plant Physiol Vol. 26: 127-158 (Volume publication date June 1975).

Varani J, Perone P, Fligiel S E, Fisher G J, Voorhees J J. Inhibition of type I procollagen production in photodamage: correlation between presence of high molecular weight collagen fragments and reduced procollagen synthesis. J Invest Dermatol. 2002 July; 119(1):122-9.

Vinck E M, Cagnie B J, Cornelissen M J, Declercq H A, Cambier D C. Increased fibroblast proliferation induced by light emitting diode and low power laser irradiation. Lasers Med. Sci. 2003; 18(2):95-9.

Webb C, Dyson M, Lewis W H. Stimulatory effect of 660 nm low level laser energy on hypertrophic scar-derived fibroblasts: possible mechanisms for increase in cell counts. Lasers Surg Med 1998; 22(5):294-301.

Weiss R A, McDaniel D H, Geronemus R G, Weiss M A. Clinical trial of a novel non-thermal LED array for reversal of photoaging: clinical, histologic, and surface profilometric results. Lasers Surg Med. 2005 February; 36(2):85-91.

Wheeland R G. Lasers for the stimulation or inhibition of wound healing. Journal of Dermatologic Surgery & Oncology 1993(19):747-52.

Whelan H T, Smits R L Jr, Buchman E V, et al. Effect of NASA light-emitting diode irradiation on wound healing, J Clin Laser Med Surg 2001 December; 19(6):305-14. Review.

Yamamoto Y, Kono T, Kotani H, Kasai S, Mito M. Effect of low-power laser irradiation on procollagen synthesis in human fibroblasts. J Clin Laser Med Surg. 1996 June; 14(3):129-32.

Yu W, Naim J O, Lanzafame R J. The effect of laser irradiation on the release of bFGF from 3T3 fibroblasts. Photochem Photobiol. 1994 February; 59(2):167-70.

Zhang Y, Song S, Fong C C, Tsang C H, Yang Z, Yang M. cDNA microarray analysis of gene expression profiles in human fibroblast cells irradiated with red light. J Invest Dermatol. 2003 May; 120(5):849-57.

What is claimed is:

1. A method of treating mammalian skin tissues for causing a predetermined physiological change in the mammalian skin tissues, said method comprising:
    applying onto the mammalian skin tissues a treatment composition of matter;
    defining a plurality of pulse trains, each pulse train including a plurality of radiation pulses having a predetermined pulse duration;
    separating the plurality of radiation pulses by an inter-pulse interval, at least one of the inter-pulse intervals being of from about 100 microseconds to about 0.5 milliseconds, at least one of the radiation pulses having a power density of 30 mW/cm$^2$ to about 100 mW/cm$^2$ for a duration of from about 100 microseconds to about 5 milliseconds;
    separating the pulse trains by an inter-pulse train interval, the inter-pulse train interval being substantially larger than the inter-pulse interval, at least two of the pulse trains being separated by an inter-pulse train interval of about 500 microseconds to about 2.25 milliseconds; and
    irradiating the mammalian skin tissues with the plurality of pulse trains under non-ablative and non-thermal conditions;
    wherein the treatment composition of matter includes a photoreactive substance and is applied in an amount sufficient to cause physiological changes within the mammalian skin tissues upon the mammalian skin tissues being irradiated.

2. The method as defined in claim 1, wherein the at least one of the radiation pulses has a wavelength of from about 400 nanometers to about 1500 nanometers.

3. The method as defined in claim 2, wherein the at least one of the radiation pulses has a duration of about 250 microseconds to about 1 millisecond.

4. The method as defined in claim 2, wherein the at least one of the radiation pulses has a duration of about 250 microseconds to about 1 millisecond and wherein the at least one of the inter-pulse intervals is from about 50 microseconds to about 0.5 millisecond.

5. The method as defined in claim 2, wherein the at least one of the radiation pulses is emitted by at least one light emitting diode (LED).

6. The method as defined in claim 2, wherein a ratio of a duration of the at least one of the radiation pulses divided by the at least one of the inter-pulse intervals is selected from the group consisting of about 0.1 to about 10 and about 0.5 to about 2.

7. The method as defined in claim 1, wherein a number of pulses within each pulse train is one of 2 to 1000 pulses, 4 to 10 pulses, and 3 to 10 pulses.

8. The method as defined in claim 1, further comprising depositing a total fluence to the mammalian skin tissues of about 4 J/cm$^2$ to about 10 J/cm$^2$ from the at least two pulse trains.

9. The method as defined in claim 1, further comprising cooling the mammalian skin tissues.

10. The method as defined in claim 1, further comprising:
    irradiating the tissue over a plurality of treatments, wherein a treatment includes one or more pulse trains; and
    providing an inter-treatment time interval between treatments.

11. The method as defined in claim 10, wherein the plurality of treatments includes from 2 to 12 treatments.

12. The method as defined in claim 1, wherein the radiation pulses are suitable for treating at least one of cutaneous textural changes induced by aging, cutaneous textural changes induced by photodamage, cutaneous textural changes induced by atrophic acne, mild erythema, dyspigmentation of the skin, hyperkeratotic lesions of the skin, hyperkeratotic diseases of the skin, inflammatory lesions of the skin, inflammatory diseases of the skin, neoplastic and pre-neoplastic diseases of the skin, granulomatous diseases of the skin, and infectious diseases of the skin.

13. A method as defined in claim 1, wherein irradiating the mammalian skin tissues includes irradiating the mammalian skin tissues with radiation including a wavelength absorbed at least in part by the photoreactive substance.

14. A method as defined in claim 13, wherein the photoreactive substance includes at least one of: a copper peptide, vitamin C, an oligopeptide, an anti-oxidant vitamin, a peptide, a chromophore, a vitamin derivative, a chlorophyll derivative, an anti-oxidant or a free radical quencher.

15. A method as defined in claim 1, wherein irradiating the mammalian skin is performed after a predetermined incubation time further to applying the treatment composition of matter, the predetermined incubation time being from about 1 minute to about 24 hours.

16. A method as defined in claim 1, wherein said method is performed in vivo on human skin.

* * * * *